United States Patent

Knute

Patent Number: 5,431,174
Date of Patent: Jul. 11, 1995

[54] METHOD OF FLUID DELIVERY AND COLLECTION

[75] Inventor: Wallace L. Knute, Leucadia, Calif.

[73] Assignee: Via Medical Corporation, San Diego, Calif.

[21] Appl. No.: 222,452

[22] Filed: Apr. 4, 1994

[51] Int. Cl.6 .............................................. A61B 19/00
[52] U.S. Cl. ................................... 128/898; 604/407
[58] Field of Search .......................... 128/897–898, 128/DIG. 6, DIG. 24; 604/87–88, 403, 407–416

[56] References Cited

U.S. PATENT DOCUMENTS

| | | |
|---|---|---|
| 1,585,911 | 4/1923 | Heublein . |
| 2,494,456 | 3/1946 | Still . |
| 4,411,662 | 10/1983 | Pearson . |
| 4,484,920 | 11/1984 | Kaufman et al. . |
| 4,637,934 | 1/1987 | White . |
| 4,645,073 | 2/1987 | Homan . |
| 5,102,408 | 4/1992 | Hamacher . |
| 5,122,129 | 6/1992 | Olson et al. . |

FOREIGN PATENT DOCUMENTS 0295204 12/1988 European Pat. Off. ............ 128/897

*Primary Examiner*—William E. Kamm
*Assistant Examiner*—J. P. Lacyk
*Attorney, Agent, or Firm*—Pretty, Schroeder Brueggemann & Clark

[57] ABSTRACT

A method of using a multi-compartment fluid assembly for calibrating an apparatus external to the assembly, while conveniently maintaining sterility. The method includes providing calibration fluid in a closed calibration container disposed within a bag that includes a connector for conveying fluids between the interior of the bag and a conventional intravascular tube. In use, fluids may be directed through the external apparatus and the intravascular tube and into the bag's interior. At an appropriate time, the calibration container is opened and the calibration fluid is withdrawn from the container to the intravascular tube, through the connector, without mixing the calibration fluid with any fluids in a remaining volume of the bag. Subsequently, the calibration fluid is transferred from the intravascular tube to the bag's interior, again through the connector.

7 Claims, 1 Drawing Sheet

METHOD OF FLUID DELIVERY AND COLLECTION

BACKGROUND OF THE INVENTION

This invention relates generally to methods for delivering and collecting fluids, and, more particularly, to a method of using a multi-compartment assembly for delivering and collecting fluids used in calibrating an external apparatus.

Systems for measuring certain chemical characteristics of fluids, e.g., concentration of certain analytes such as ions, gases and metabolites in human blood, can take the form of blood chemistry diagnostic systems integrated into infusion fluid delivery systems of the kind commonly used in hospital patient care. Such fluid delivery systems infuse nutrients, medications and the like directly into the patient at a controlled rate and in precise quantities for maximum effectiveness. Infusion fluid delivery systems are connected to a patient at an intravascular (IV) port, in which a hollow needle/catheter combination, with an exposed female luer connector, is inserted into a blood vessel of the patient and thereafter an infusion fluid is introduced into the blood vessel at a controlled rate, typically using a peristaltic pump. Blood chemistry monitoring systems that are combined with infusion delivery systems of this kind use the IV port to periodically withdraw a blood sample, perform measurements of blood ion concentrations and the like, and then discard the blood or reinfuse it into the patient. The system then resumes delivery of the infusion fluid.

Such combined infusion fluid delivery and blood chemistry monitoring systems include an intravascular tube and catheter through which the infusion fluid is provided to the patient and blood samples are withdrawn. The intravascular tube incorporates an electrode array having sensors (e.g., electrochemical, optical, etc.) that are periodically exposed to the blood samples and thereby provide signals to an analyzer for conversion into corresponding blood chemistry data. A control unit periodically halts delivery of the infusion fluid for a brief interval, during which time a blood sample is withdrawn from the patient into the intravascular tube and routed to the sensor array, which then generates the electrical signals. After the electrical signals have been received by the analyzer, the control unit disposes of the blood or reinfuses it into the patient, and the flow of infusion fluid is resumed.

When electrochemical sensors are employed, the electrode array typically includes a reference electrode and a plurality of sensor electrodes that are each sensitive to a particular ion of interest. An example of an electrode array of this type is shown in U.S. Pat. No. 5,220,920. When an electrode array of this type is used to measure the concentration of various gases in a parent's blood, it is important that the electrode array be stabilized and that the infusion fluid have a temperature very close to the normal patient temperature. This ordinarily necessitates a lengthy stabilization and warm-up period prior to the infusion of fluids into the patient.

Accordingly, during the stabilization and warm-up period, typically about 30 minutes, the heated infusion fluid is passed through the electrode array and then discarded. Further, near the end of the period, a calibration fluid must be passed through the electrode array, to properly calibrate the sensor electrodes, and then discarded. Throughout this entire procedure, sterility must be maintained.

It should therefore be appreciated that there is a need for a method for supplying, collecting and storing calibration and infusion fluids that maintains a sterile environment through the warm-up and calibration process. The present invention fulfills this need.

SUMMARY OF THE INVENTION

This invention resides in a method of using a multi-compartment assembly for delivering and collecting fluids used in calibrating an apparatus. The method is particularly useful as part of a procedure to warm-up and calibrate sensors in an infusion delivery-based blood chemistry monitor prior to use.

More particularly, the method of the present invention includes providing calibration fluid in a closed calibration container disposed within a bag that includes a connector for conveying fluids between the interior of the bag and a conventional intravascular tube. The calibration container is opened and the calibration fluid is withdrawn from the container to the intravascular tube, through the connector, without mixing the calibration fluid with any fluids in a remaining volume of the bag. Subsequently, the calibration fluid is transferred from the intravascular tube to the bag's interior, again through the connector.

In other, more detailed features of the invention, the multi-compartment fluid assembly also includes a sampling tube within the bag, for conveying fluids to the connector. The calibration fluid is transferred from the calibration container to the intravascular tube by inserting the sampling tube into the calibration container and transferring the calibration fluid through the sampling tube to the connector. Other features of the invention include providing one or more additional calibration fluids in additional calibration container(s) located in the bag, and delivering and collecting the additional calibration fluid using the same method as used for the first calibration fluid. Another feature includes transferring of infusion fluid into the bag's interior through the connector, prior to opening the first calibration container.

Other features and advantages of this invention should become apparent from the following description of the preferred method, taken in conjunction with the accompanying drawing, which illustrates, by way of example, the principles of the invention.

DESCRIPTION OF THE PREFERRED METHOD

The following description of the preferred method of the invention is not to be taken in a limiting sense, but is made merely for the purpose of illustrating the general principles of the invention. The description is of the best mode presently contemplated for carrying out the invention.

Figure 1:
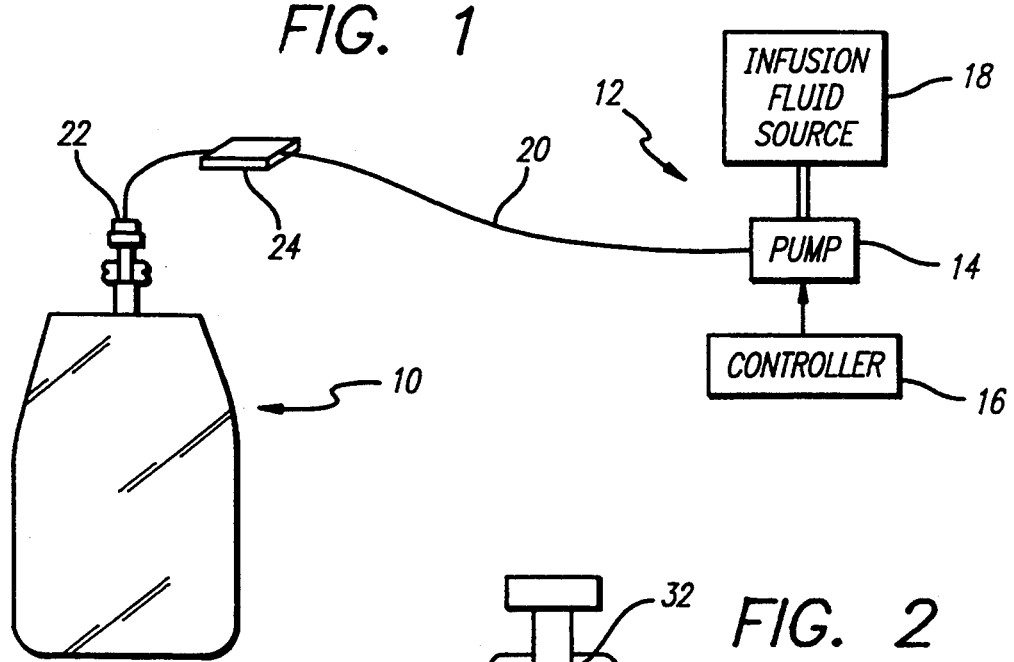
FIG. 1 is a schematic diagram of a multi-compartment fluid assembly shown connected to a combination infusion fluid delivery and blood chemistry analysis system for warm-up and calibration of the system.

With reference to FIG. 1, there is shown a multi-compartment fluid assembly 10 for use in effecting the sterile transfer of calibration fluids to and from an infusion fluid delivery and blood chemistry analysis system 12. An infusion pump 14, under the control of a controller 16, pumps infusion fluid from a fluid source 18 through the analysis system via an intravascular tube 20 and to a male luer connector 22. The pump and controller may be integrated together as a unit. An electrode array 24 is located in the middle of the intravascular tube and arranged such that the infusion fluid passes through it on its way to the male luer connector. During warm-up and calibration of the analysis system, the male luer connector is connected to the multi-compartment fluid assembly 10. Afterward, the male luer connector is inserted in the female luer connector at the end of an IV port (not shown) inserted in the patient's arm.

During use of the analysis system 12 on a patient, the controller 16 periodically conditions the pump 14 to interrupt its pumping of the infusion fluid to the patient and, instead, to reverse direction and draw a blood sample from the patient. This blood sample is drawn rearwardly through the intravascular tube 20 as far as the electrode array 24, to allow certain characteristics of the blood to be measured. After the measurements have been completed, the pump reinfuses the blood sample back into the patient and then resumes pumping the infusion fluid.

Figure 2:
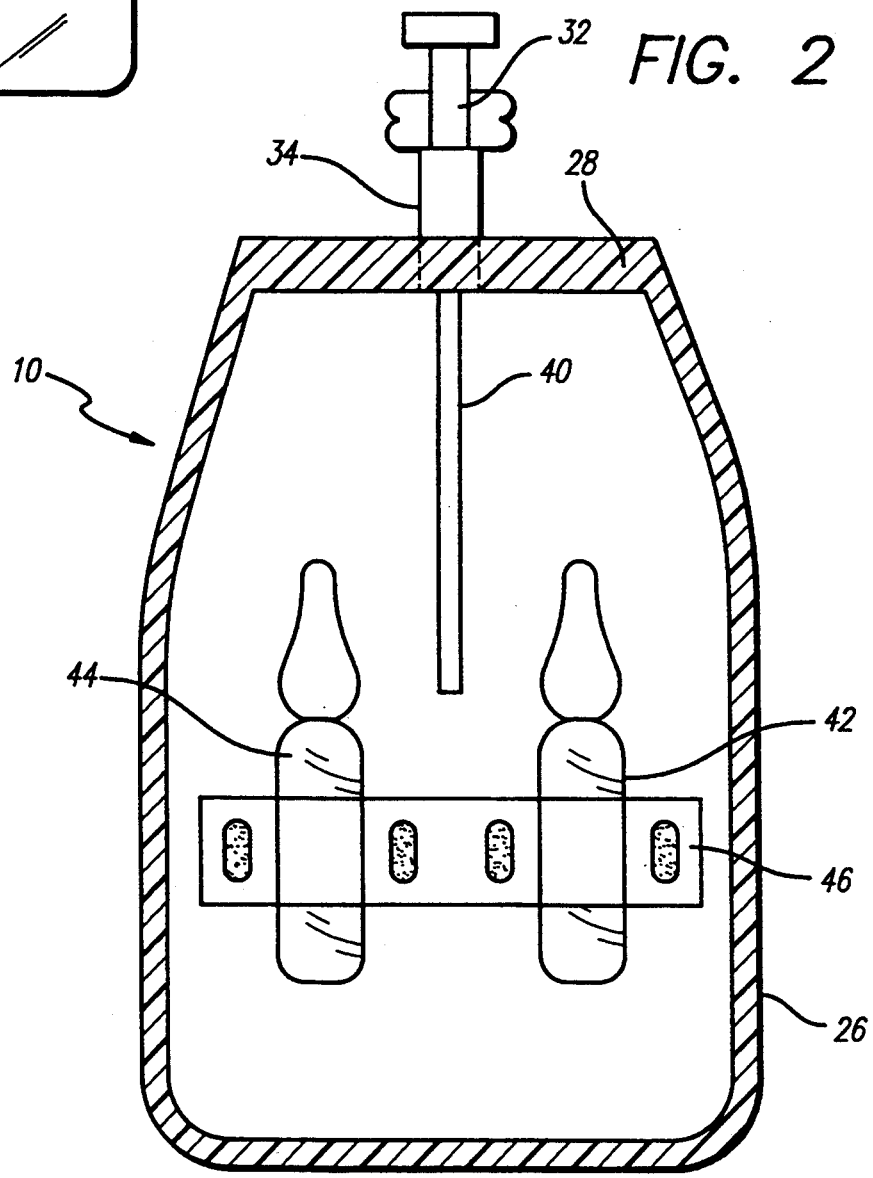
FIG. 2 is a cross-sectional view of a multi-compartment fluid assembly used in performing the preferred method of the invention.

The multi-compartment fluid assembly 10 is depicted in greater detail in FIG. 2. The assembly includes a bag 26 that is preferably formed of plastic sheet material, which may be either in the form of a sleeve or in the form of two plastic sheets that are peripherally heat sealed to create a seam 28. The plastic sheets may be made of any appropriate plastic material. A preferred material is high tear strength polyvinyl chloride (PVC). Moreover, the bag is preferably transparent, to permit the user to easily view its contents.

The bag 26 includes a connector for fluid communication between the interior of the bag and the male luer connector of a conventional intravascular tube, such as the intravascular tube 20 of FIG. 1. In the preferred method, the connector is a female luer connector 32 that is attached to a PVC connecting tube 34 which passes through and is heat sealed to an upper portion of the bag's seam 28. The multi-compartment fluid assembly 10 also includes a sampling tube 40 located within the bag 26 and in fluid communication with the female luer connector 32 through the connecting tube 34. In the preferred method, the sampling tube is a rigid tube that extends downwardly from the connecting tube, in a portion of the bag's interior. A suitable filter material (not shown) may be disposed in the connector 32, to prevent debris from entering the bag 26.

Also in the preferred method, first and second closed calibration containers 42 and 44, respectively, are disposed within the interior of the bag 26. The containers preferably take the form of breakable glass ampules. These calibration containers store calibration fluids that can be used to calibrate the electrode array 24. The calibration containers are secured within the bag by PVC tubes 46 and 48 that are heat sealed on the side of the bag. The tubes assist in securing the containers when the multi-compartment fluid assembly 10 is being transported and in use. This is particularly important when the calibration containers are formed of glass or otherwise are susceptible to breakage by hitting each other. A reinforced aperture 50 at the end of the bag opposite the female luer connector 32 allows the assembly 10 conveniently to be suspended on a hook (not shown).

In the preferred method of the present invention, the multi-compartment fluid assembly 10 described above is used to calibrate and warm-up the infusion fluid delivery and blood chemistry analysis system 12 in a sterile environment. Initially, the male luer connector 22 is inserted into the bag's female luer connector 32 to provide fluid communication between the interior of the bag 26 and the intravascular tube 20.

Stabilizing the electrode array 24 and warming up the infusion fluid prior to infusion into a patient, typically takes about 30 minutes. During this warm-up period, fluid is being pumped by the infusion pump 14 through the electrode array 24. The heated infusion fluid is transferred from the intravascular tube 20 and into the interior of the bag 26 through the male luer connector 22, the female luer connector 32 and the connector tube 34. The infusion fluid can be stored in the sealed bag and discarded later.

Each of the electrodes in the electrode array 24 includes an electrochemical sensor which develops an electrical signal that varies in accordance with a predetermined parameter of the blood to which the electrochemical sensor is sensitive. Examples of parameters that are commonly measured in this fashion include pH, concentrations of sodium, potassium and calcium, and glucose, hematocrit, and partial pressures of oxygen ($pO_2$) and carbon dioxide ($pCO_2$). However, prior to measurement of these parameters, a special calibration fluid must be passed through the electrode array 24 so that the electrodes can be properly calibrated.

Accordingly, in the preferred method of the present invention, the multi-compartment fluid assembly 10 is provided with the closed first calibration container 42 and the closed second calibration container 44, containing a first calibration fluid and a second calibration fluid, respectively. When it is desired to pass a calibration fluid through the electrode array 24, generally at a time near the end of the warm-up period, the first calibration container is opened. Then the first calibration fluid is withdrawn from the first calibration container to the intravascular tube 20, through the connecting tube 34 and the female luer connector 32, without mixing the first calibration fluid with the infusion fluid in a remaining volume of the bag.

More specifically, after the first calibration container 42 has been opened, the sampling tube 40 is inserted into the first calibration container and the first calibration fluid is withdrawn through the sampling tube to the connector tube 34 and the female luer connector 32. In the preferred method, the controller 16 conditions the pump 14 to reverse direction and draw the first calibration fluid from the first calibration container. This calibration fluid is drawn rearwardly through the intravascular tube 20 as far as the electrode array 24, to calibrate the sensor electrodes in the array. The filter material disposed in the female luer connector 32 prevents any minute glass shards from the broken calibration container 42 from exiting the bag's interior.

After sufficient time to enable the electrode array 24 to be calibrated, the controller 16 conditions the pump 14 to reverse direction again and transfer the first calibration fluid from the intravascular tube 20 through the male luer connector 22 to the bag's interior through the female luer connector 32 and the connector tube 34.

If a second calibration is required, the second calibration container 44 is opened and the second calibration fluid is withdrawn from the second calibration container to the intravascular tube 20, through the connecting tube 34 and the female luer connector 32, without mixing the second calibration fluid with the infusion fluid in a remaining volume of the bag. Again, after sufficient time to enable the electrode array 24 to be calibrated, the second calibration fluid is transferred from the intravascular tube 20 through the male luer connector 22 to the bag's interior through the female luer connector 32 and the connector tube 34.

After the sensor array 24 has been properly calibrated and the warm-up period has concluded, the male luer connector 22 is withdrawn from the female luer connector 32 and inserted into the patient's IV port (not shown). The multi-compartment fluid assembly 10, with its charge of used infusion fluid and calibration fluid, is then disposed of.

It should be appreciated from the foregoing description that the present invention provides an improved method for delivering and collecting fluids used in calibrating an apparatus. Infusion fluid passed through the infusion fluid delivery and blood chemistry analysis system 12 can be efficiently collected and disposed of in a sealed bag. Additionally, the electrode array 24 is fully calibrated while maintaining complete sterility of the calibration fluid and the sensor electrodes.

Although the invention has been described in detail with reference to the presently preferred method, those of ordinary skill in the art will appreciate that various modifications can be made without departing from the invention. Accordingly, the invention is defined only by the following claims.

I claim:

1. A method of using a multi-compartment fluid assembly for calibrating an apparatus external to the assembly, comprising:
   providing a calibration fluid in a closed calibration container disposed within a bag, the bag having a connector for fluid communication between the interior of the bag and a conventional intravascular tube;
   opening the calibration container;
   withdrawing the calibration fluid from the calibration container to the intravascular tube through the connector, without mixing the calibration fluid with any fluids in a remaining volume of the bag; and
   subsequently transferring the calibration fluid from the intravascular tube to the bag's interior, through the connector.

2. The method of claim 1, wherein:
   the multi-compartment fluid assembly further includes a sampling tube disposed within the bag, in fluid communication with the connector; and
   withdrawing the calibration fluid from the calibration container to the intravascular tube includes
   inserting the sampling tube into the calibration container, and
   withdrawing the calibration fluid through the sampling tube to the connector.

3. The method of claim 1, and further comprising:
   providing one or more additional calibration fluid in one or more additional closed calibration containers disposed within the bag;
   opening the one or more additional calibration containers;
   withdrawing the one or more additional calibration fluids from the one or more additional calibration containers to the intravascular tube through the connector, without mixing the calibration fluids with any fluids in the remaining volume of the bag; and
   subsequently transferring the one or more additional calibration fluids from the intravascular tube to the bag's interior, through the connector.

4. The method of claim 1, and further comprising transferring an infusion fluid from the intravascular tube to the bag's interior, through the connector, prior to opening the calibration container.

5. A method of using a multi-compartment fluid assembly for calibrating an infusion fluid delivery and blood chemistry analysis system connected to a fluid source containing infusion fluid, the system having a pump, an intravascular tube with a connector, and an electrode array for measuring characteristics of blood entering the system, comprising:
   providing a calibration fluid in a closed calibration container disposed within a bag, the bag having a connector for fluid communication between the interior and the exterior of the bag;
   mating the intravascular tube's connector with the bag's connector;
   pumping the infusion fluid from the fluid source through the intravascular tube and the electrode array;
   transferring the infusion fluid from the intravascular tube to the bag's interior, through the mated connectors of the intravascular tube and the bag;
   opening the calibration container;
   withdrawing the calibration fluid from the calibration container to the intravascular tube through the mated connectors of the intravascular tube and the bag, without mixing the calibration fluid with the infusion fluid in the bag;
   calibrating the electrode array with the calibration fluid; and
   subsequently transferring the calibration fluid from the intravascular tube to the bag's interior, through the mated connectors of the intravascular tube and the bag.

6. The method of claim 5, wherein:
   the multi-compartment fluid assembly further includes a sampling tube disposed within the bag, in fluid communication with the bag's connector; and
   withdrawing the calibration fluid from the calibration container to the intravascular tube includes
   inserting the sampling tube into the calibration container, and
   withdrawing the calibration fluid through the sampling tube to the connector.

7. The method of claim 5, and further comprising:
   providing one or more additional calibration fluids in one or more additional closed calibration containers disposed within the bag;
   opening the one or more additional calibration containers;
   withdrawing the one or more additional calibration fluids from the second calibration container to the intravascular tube through the mated connectors of the intravascular tube and the bag, without mixing the calibration fluids with the infusion fluid in the bag;
   calibrating the electrode array with the one or more additional calibration fluids; and
   subsequently transferring the one or more additional calibration fluids from the intravascular tube to the bag's interior, through the mated connectors of the intravascular tube and the bag.

* * * * *